(12) United States Patent
Nakano et al.

(10) Patent No.: US 8,338,404 B2
(45) Date of Patent: Dec. 25, 2012

(54) COMPOSITION AND METHOD FOR REDUCING ALLERGEN

(75) Inventors: Tetsuo Nakano, Tokyo (JP); Hideo Kawabe, Tokyo (JP); Keiichirou Inui, Hyogo (JP); Kouichi Waki, Kyoto (JP)

(73) Assignees: Kyowa Hakko Bio Co., Ltd., Toky (JP); Sumika Enviro-Science Co., Ltd., Hyogo (JP)

( * ) Notice: Subject to any disclaimer, the term of this patent is extended or adjusted under 35 U.S.C. 154(b) by 277 days.

(21) Appl. No.: 11/853,401

(22) Filed: Sep. 11, 2007

(65) Prior Publication Data

US 2009/0069403 A1  Mar. 12, 2009

(51) Int. Cl.
*A01N 43/00* (2006.01)
*A61K 31/33* (2006.01)

(52) U.S. Cl. .......................... 514/183; 514/423

(58) Field of Classification Search .............. None
See application file for complete search history.

(56) References Cited

U.S. PATENT DOCUMENTS

| | | | | |
|---|---|---|---|---|
| 3,997,559 A | * | 12/1976 | Coirre et al. ................. | 548/403 |
| 6,117,440 A | * | 9/2000 | Suh et al. ...................... | 424/407 |
| 2003/0185864 A1 | | 10/2003 | Kobayashi et al. | |
| 2006/0034781 A1 | * | 2/2006 | Takahashi et al. ............. | 424/49 |
| 2008/0083337 A1 | * | 4/2008 | Yamanaka et al. ............. | 96/222 |

FOREIGN PATENT DOCUMENTS

| | | | |
|---|---|---|---|
| JP | 61-44821 | | 3/1986 |
| JP | 6-279273 | | 10/1994 |
| JP | 2000-005531 | | 1/2000 |
| JP | 2002-370996 | | 12/2002 |
| JP | 2003-79756 | | 3/2003 |
| JP | 2003079756 A | * | 3/2003 |
| JP | 2004-83844 | | 3/2004 |
| JP | 2004083844 A | * | 3/2004 |
| JP | 2007-070543 | | 3/2007 |
| JP | 2007070543 A | * | 3/2007 |
| WO | 02/06225 | | 1/2000 |
| WO | 00/51561 | | 9/2000 |
| WO | 2004/028531 | | 4/2004 |
| WO | 2004/039368 | | 5/2004 |
| WO | WO 2006040349 A1 | * | 4/2006 |
| WO | WO 2006120851 A1 | * | 11/2006 |

OTHER PUBLICATIONS

Shaw et al Atopic dermatitis in the dog, internet archive 1998, accessed on Apr. 8, 2010.*
Agnes et al "chemical principles of textiles conservation" 1998, ISBN 0 7506 2620 8.*
Gerard et al "A monthly newsletter by RSAF medical services/CAMO's office" HF Feb. 2001.*
Machine translation of WO2006120851.*
Harris, et al., "Effects of Oxaceprol on the Microcirculation in Ischemia/Reperfusion Injury", Eur. J. Med. Res., vol. 3 (1998) 182-88.
Harrison's Principles of Internal Medicine, 15th ed. (2001) 309.
Atopic Dermatits (2010) http://en.wikipedia.org/wiki/Atopic_dermatitis, 1-9.

* cited by examiner

*Primary Examiner* — Brandon Fetterolf
*Assistant Examiner* — Jean Cornet
(74) *Attorney, Agent, or Firm* — Fitzpatrick, Cella, Harper & Scinto

(57) ABSTRACT

This invention relates to an allergen-reducing composition comprising a hydroxyproline derivative, a polymer thereof, or a salt of such a derivative or polymer, which is capable of reducing the allergenicity of mites, pollens, or other allergens and is capable of imparting functions of reducing allergenicity to fibers or textiles such as a carpet, a tatami mat, a bed cloth, a curtain, clothing, a stuffed animal, a mask, a filter material, or a dust bag for an electric vacuum cleaner without discoloration; and a method for reducing allergens using such composition.

13 Claims, No Drawings

COMPOSITION AND METHOD FOR REDUCING ALLERGEN

BACKGROUND OF THE INVENTION

1. Field of the Invention

The present invention relates to an allergen-reducing composition that reduces the allergenicity of allergens such as mites or pollens or that imparts functions of reducing allergenicity to fibers or textiles.

2. Background Art

As the causes of allergic diseases such as asthma or atopic dermatitis, mites which live indoors, and pollens, pet hair, mold, and the like are known.

Mites appear in many forms, such as Cheyletidae or acarid mites. Among such mites, *Dermatophagoides farinae* and *Dermatophagoides pteronyssinus* are considered to be major factors that induce mite allergies. Not only such mite bodies become allergenic factors that induce allergies, dead mites or mite feces also become potent allergens. Molds are likely to develop in damp places. When molds are inhaled into the lungs, they become allergens. Pollens of cedar, Japanese cypress, ragweed, timothy, zelkova, mugwort, vernal grass, and the like are known to become allergens.

At present, medication is mainly employed for treatment of allergy patients. The removal of allergens from the living environments of patients is an effective means for protecting patients from exposure to allergens.

While masks are used for preventing inhalation of cedar pollen or the like, pollen that has adhered to masks does not lose its allergenicity, and such pollen may be disadvantageously inhaled upon reentrainment thereof.

Meanwhile, indoor textiles, such as tatami mats, carpets, bedclothes, and curtains, are often hotbeds of mite growth. Examples of methods for removing allergens such as mites from such products include suctioning with the use of a vacuum cleaner, removal of mites with the use of an air purification system, and use of extremely dense covers for bedclothes. However, the amount of an allergen that can be removed by suctioning with the use of a vacuum cleaner is limited, and allergens may be disadvantageously reentrained at the time of disposal of a dust bag. Also, an air purification system can only remove airborne allergens. Further, dense covers for bedclothes can block internal allergens, but they cannot eliminate external allergens.

Examples of methods for reducing or eliminating allergenicity include methods involving the use of an agent for reducing allergens, such as tannic acid (JP Patent Publication (kokai) No. 61-44821 A (1986)) or tea extracts, hydroxyapatite, epicatechin, epigallocatechin, epicatechin gallate, epigallocatechin gallate, gallic acid, and ester compounds of gallic acid and a $C_{1-4}$ alcohol (JP Patent Publication (kokai) No. 6-279273 A (1994)). Such agent for reducing allergens disadvantageously develops color or becomes discolored over time when such agent is brought into contact with fibers or textiles. Also, agents for reducing allergens that use aromatic hydroxy compounds (JP Patent Publication (kokai) No. 2003-79756 A) or polysaccharide derivatives comprising, as main chains, cellulose ether or starch ether (JP Patent Publication (kokai) No. 2004-83844 A) are known. These agents, however, are poor in terms of reactivity with allergens, their effects to reduce allergens are insufficient, and they are not metabolized in vivo.

An N-acylated derivative of hydroxyproline is known to be used as an agent for preventing atopic dermatitis (WO 2004/039368), an agent for suppressing skin aging or an agent for improving skin quality (WO 00/51561), or a wound-treating agent (WO 2004/028531); however, whether or not such derivative directly acts on allergens to reduce allergenicity is not known.

SUMMARY OF THE INVENTION

An object of the present invention is to provide an allergen-reducing composition that does not become discolored, is safe, and exhibits low toxicity for reducing the allergenicity of allergens such as mites or pollens or for imparting functions of reducing allergenicity to fibers or textiles.

The subject matters of the present invention are as follows.

(1) An allergen-reducing composition comprising a hydroxyproline derivative represented by formula (I):

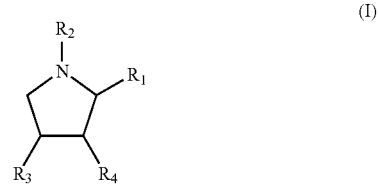

wherein $R_1$ represents hydrogen, carboxy, acyl, or alkoxycarbonyl; $R_2$ represents hydrogen or acyl; and $R_3$ and $R_4$ each represent hydrogen or hydroxy, provided that either $R_3$ or $R_4$ represents hydroxy, a polymer thereof, or a salt of such a derivative or polymer.

(2) The allergen-reducing composition according to item (1), wherein, in formula (I), $R_1$ represents carboxy; $R_2$ represents acetyl; $R_3$ represents hydroxy; and $R_4$ represents hydrogen.

(3) The allergen-reducing composition according to item (1) or (2), wherein the content of the hydroxyproline derivative represented by formula (I), a polymer thereof, or a salt of such a derivative or polymer is 0.01% to 30% by weight.

(4) The allergen-reducing composition according to any of items (1) to (3), which further comprises at least 1 member selected from the group consisting of a nonionic surfactant, an anionic surfactant, a cationic surfactant, an fungicide, an antibacterial agent, a miticide, an NOX removing agent, a humectant, a fragrance, and a binder.

(5) An aerosol or spray comprising the allergen-reducing composition according to any of items (1) to (4).

(6) A fiber or textile comprising the allergen-reducing composition according to any of items (1) to (4) adhered or fixed thereon.

(7) A mask comprising the allergen-reducing composition according to any of items (1) to (4) adhered or fixed thereon.

(8) A method for reducing allergen comprising preparing the allergen-reducing composition according to any of items (1) to (4) and bringing such composition into contact with an allergen.

(9) The method according to item (8), wherein the allergen is derived from at least 1 member selected from the group consisting of mites, plants, pets, cockroaches, feather, and molds.

(10) A method for preparing a material or product capable of reducing allergenicity comprising preparing the allergen-reducing composition according to any of items (1) to (4) and allowing such composition to adhere or fix on at least 1 member selected from the group consisting of a fiber, a textile, a building material, a rubber, a paper, a resin, and a plastic.

(11) A method for imparting a function of reducing allergenicity comprising preparing the allergen-reducing composition according to any of items (1) to (4) and allowing such composition to adhere or fix on an object to be treated.

Use of the composition of the present invention enables the reduction of allergenicity of mite, pollen, or other allergens. Also, fibers or textiles capable of reducing allergenicity can be provided by treating the fibers or textiles with the composition.

DETAILED DESCRIPTION

Each group in the hydroxyproline derivative represented by formula (I) used in the present invention is defined as follows. An acyl group is a linear or branched aliphatic acyl group having preferably 1 to 20 carbon atoms and more preferably 1 to 10 carbon atoms. Specific examples thereof include formyl, acetyl, propionyl, butyryl, isobutyryl, valeryl, isovaleryl, pivaloyl, hexanoyl, heptanoyl, octanoyl, nonanoyl, decanoyl, undecanoyl, dodecanoyl, oleoyl, linoleoyl, palmitoyl, and stearoyl groups, with acetyl, propionyl, butyryl, and isobutyryl groups being particularly preferable.

An alkoxy moiety in the alkoxycarbonyl group is preferably a linear or branched alkoxy group having 1 to 10 carbon atoms. Examples thereof include methoxy, ethoxy, propoxy, and butoxy groups.

The hydroxyproline derivative represented by formula (I) comprises a variety of isomers without limitation. When $R_3$ and $R_4$, which are different from each other, each represent hydrogen or hydroxy and $R_1$ represents carboxy, acyl, or alkoxycarbonyl, for example, a cis-form, trans-form, or cis-trans mixture can be used. Also, any of an optically active D- or L-form or a racemic modification may be used.

In the hydroxyproline derivative represented by formula (I), examples of hydroxyproline derivative wherein $R_1$ represents carboxy; $R_2$ represents hydrogen; and $R_3$ and $R_4$, which are different from each other, each represent hydrogen or hydroxy include cis-4-hydroxy-L-proline, cis-4-hydroxy-D-proline, trans-4-hydroxy-D-proline, trans-4-hydroxy-L-proline, cis-3-hydroxy-L-proline, cis-3-hydroxy-D-proline, trans-3-hydroxy-D-proline, and trans-3-hydroxy-L-proline.

Hydroxyproline is an amino acid species that is extensively present in nature as a major constitutive amino acid component in collagen or as a constitutive amino acid of elastin. For example, hydroxyproline can be prepared by subjecting collagen derived from an animal such as a pig or cow to acid hydrolysis and purifying the product in accordance with a conventional technique.

Trans-4-hydroxy-L-proline can be prepared using proline-4-hydroxylase (JP Patent Publication (kokai) No. 7-313179 (A) (1995)) isolated from microorganisms of the genus *Amycolatopsis* or *Dactylosporangium*. Also, cis-3-hydroxy-L-proline can be prepared using proline-3-hydroxylase (JP Patent Publication (kokai) No. 7-322885 (A) (1995)) isolated from microorganisms of the genus *Streptomyces* (Bioindustry, Vol. 14, No. 31, 1997).

The hydroxyproline derivative represented by formula (I), for example, an N-acylated derivative of hydroxyproline wherein $R_1$ represents carboxy; $R_2$ represents acyl; and $R_3$ and $R_4$, which are different from each other, each represent hydrogen or hydroxy, can be prepared in accordance with a conventional technique. For example, an N-acylated derivative of hydroxyproline can be prepared preferably by converting a linear or branched and saturated or unsaturated fatty acid having 1 to 20 carbon atoms into a halide such as chloride or bromide using a halogenating agent such as thionyl chloride or phosgene and condensing the product with the aforementioned hydroxyproline, or by converting a fatty acid into acid anhydride, and allowing the product to react with the aforementioned hydroxyproline.

Examples of fatty acids that can be used include formic acid, acetic acid, propionic acid, butyric acid, isobutyric acid, valeric acid, isovaleric acid, pivalic acid, hexanoic acid, heptanoic acid, octanoic acid, nonanoic acid, decanoic acid, undecanoic acid, dodecanoic acid, oleic acid, linoleic acid, palmitic acid, and stearic acid. Such fatty acid is used alone or in combinations of two or more.

A method for producing an N-acylated derivative of hydroxyproline via an acid halide is exemplified below.

A fatty acid is dispersed in a solvent such as methylene chloride, chloroform, carbon tetrachloride, benzene, toluene, xylene, n-hexane, etc., 1 to 5 equivalent(s) of a halogenating agent is added thereto, and the reaction is allowed to proceed to obtain a fatty acid halide. Thereafter, hydroxyproline is dissolved or dispersed in a solvent and, while the resulting solution is kept at 5° C. to 70° C., the above fatty acid halide is added in an amount of 0.3 to 3.0 equivalents to hydroxyproline to conduct an acylation reaction whereupon an N-acylated derivative of hydroxyproline is produced.

Examples of the solvent used for the acylation reaction include water, methanol, ethanol, isopropanol, isobutanol, acetone, toluene, tetrahydrofuran, ethyl acetate, N,N-dimethylformamide, dimethyl sulfoxide, etc. and each of them may be used solely or as a mixture. In dissolving or dispersing hydroxyproline in a solvent, 0.8 to 2.0 equivalents of an alkaline substance such as sodium hydroxide, potassium hydroxide, etc. relative to hydroxyproline may be dissolved or dispersed in a solvent according to need.

Examples of N-acylated derivatives of hydroxyproline include N-acetyl-cis-4-hydroxy-L-proline, N-acetyl-cis-4-hydroxy-D-proline, N-acetyl-cis-3-hydroxy-L-proline, N-acetyl-cis-3-hydroxy-D-proline, N-acetyl-trans-4-hydroxy-L-proline, N-acetyl-trans-4-hydroxy-D-proline, N-acetyl-trans-3-hydroxy-L-proline, N-acetyl-trans-3-hydroxy-D-proline, N-propionyl-cis-4-hydroxy-L-proline, N-propionyl-cis-4-hydroxy-D-proline, N-propionyl-cis-3-hydroxy-L-proline, N-propionyl-cis-3-hydroxy-D-proline, N-propionyl-trans-4-hydroxy-L-proline, N-propionyl-trans-4-hydroxy-D-proline, N-propionyl-trans-3-hydroxy-L-proline, N-propionyl-trans-3-hydroxy-D-proline, N-butyryl-cis-4-hydroxy-L-proline, N-butyryl-cis-4-hydroxy-D-proline, N-butyryl-cis-3-hydroxy-L-proline, N-butyryl-cis-3-hydroxy-D-proline, N-butyryl-trans-4-hydroxy-L-proline, N-butyryl-trans-4-hydroxy-D-proline, N-butyryl-trans-3-hydroxy-L-proline, N-butyryl-trans-3-hydroxy-D-proline, N-isobutyryl-cis-4-hydroxy-L-proline, N-isobutyryl-cis-4-hydroxy-D-proline, N-isobutyryl-cis-3-hydroxy-L-proline, N-isobutyryl-cis-3-hydroxy-D-proline, N-isobutyryl-trans-4-hydroxy-L-proline, N-isobutyryl-trans-4-hydroxy-D-proline, N-isobutyryl-trans-3-hydroxy-L-proline, and N-isobutyryl-trans-3-hydroxy-D-proline.

A polymer of the hydroxyproline derivative represented by formula (I) is not particularly limited, provided that such polymer is composed of two or more of the hydroxyproline derivatives represented by formula (I). A polymer represented by formula (II) is preferable:

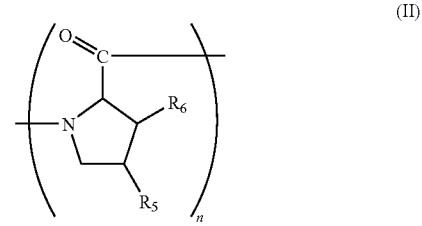

(II)

wherein n is a number between 2 and 50; and n number of $R_5$ and $R_6$, which are the same or different, each represent hydrogen or hydroxy.

A polymer represented by formula (II) can be prepared by, for example, the thermal polycondensation reaction described in Analytical Methods of Protein Chemistry, pp. 127-154, Pergamon Press, Oxford, 1966.

Examples of a salt of the hydroxyproline derivative represented by formula (I) or of the polymer thereof include a salt with alkaline metal such as sodium, potassium, or lithium, a salt with alkaline earth metal such as calcium or magnesium, an addition salt with amine such as ammonium ion, monoethanolamine, diethanolamine, or triethanolamine, and an addition salt with a basic amino acid such as arginine or lysine.

When the preparation of a salt of the hydroxyproline derivative represented by formula (I) or of the polymer thereof is intended and when such derivative or polymer is obtained in the form of a salt, the product itself may be purified. When it is prepared in a free form, it may be dissolved or suspended in an adequate solvent and a base may be added thereto to form a salt.

Purification may be carried out in accordance with a conventional method, such as crystallization or chromatography.

In the allergen-reducing composition according to the present invention, the content of the hydroxyproline derivative represented by formula (I), the polymer thereof, or the salt of the derivative or polymer may be at any level. It is preferably 0.01% to 30% by weight, in order to act on the allergen to reduce or eliminate the capacity thereof to induce allergic reactions. When used in the form of an aerosol or spray, for example, such content is preferably 0.01% to 10% by weight, and more preferably 0.1% to 3% by weight. When used as a processing agent into fibers or textiles, for example, such content is preferably 0.01% to 30% by weight, and more preferably 0.1% to 20% by weight.

The allergen-reducing composition of the present invention may be any of a liquid, paste, powder, or other forms, provided that such composition can be processed or adhered or fixed to fibers or textiles in the presence of allergens. A liquid form is preferable from the viewpoint of ease of handling.

The dosage form of the allergen-reducing composition of the present invention may be any of a water dispersible powder, emulsion, oil, aerosol or spray, mist, an embrocation, a powder, or granule. From the viewpoint of ease of handling, a liquid dosage, such as a water dispersible powder, emulsion, oil, or aerosol or spray is preferable, with the use as an aerosol or spray being further preferable.

As the solvent used for preparing the allergen-reducing composition of the present invention, an adequate solvent for dissolving or dispersing the hydroxyproline derivative represented by formula (I), a polymer thereof, or a salt of such a derivative or polymer can be used solely or in combination.

Examples of solvents that can be adequately used include, but are not particularly limited to, polar solvents, such as water, methyl alcohol, ethyl alcohol, isopropyl alcohol, benzyl alcohol, acetic acid, acetone, dimethylformamide, dimethylacetamide, dimethyl sulfoxide, ethylene glycol, propylene glycol, diethylene glycol, triethylene glycol, dipropylene glycol, hexylene glycol, polyethylene glycol, glycerine, ethylene glycol monomethyl ether, ethylene glycol monoethyl ether, diethylene glycol monomethyl ether, diethylene glycol monoethyl ether, diethylene glycol monobutyl ether, diethylene glycol monoethyl ether acetate, γ-butyrolactone, or sulfolane, and non-polar solvents, such as dimethylnaphthalene, dodecylbenzene, liquid paraffin, isophorone, kerosine, dibutyl adipate, diethyl phthalate, diethylene glycol monobutyl ether acetate, propylene carbonate, coconut oil, rapeseed oil, cottonseed oil, castor oil, or soybean oil. In general, polar solvents, such as water, an alcohol, or a glycol ether, are used.

The allergen-reducing composition of the present invention may comprise, for example, a nonionic surfactant, anionic surfactant, cationic surfactant, fungicide, or antibacterial agent.

Examples of nonionic surfactants include polyoxyethylene alkyl phenyl ether, polyoxyethylene styryl phenyl ether, polyoxyethylene alkyl ether, polyoxyethylene alkenyl ether, sorbitan fatty acid ester, and polyoxyethylene sorbitan fatty acid ester.

Examples of anionic surfactants include alkylbenzene sulfate, polyoxyethylene alkyl ether sulfate, polyoxyethylene alkylphenyl ether sulfate, and dialkyl sulfosuccinate.

Examples of cationic surfactants include an aliphatic amine salt and a quaternary ammonium salt thereof.

Such nonionic, anionic, or cationic surfactants may be used alone or in combinations of two or more.

An fungicide or an antibacterial agent is not particularly limited, provided that such agent has the fungicidal or antibacterial effects. Examples thereof include 5-chloro-N-methyl isothiazolone, methylene bisthiocyanate, 2-bromo-2-nitropropane-1,3-diol, glutaraldehyde, iodopropynyl butylcarbamate, pyridinethiol-N-oxide zinc salt, 1,2-benzisothiazolone, 1,2-dibromo-2,4-dicyanobutane, chlorhexidine gluconate, 2-isopropyl-5-methylphenol, 3-methyl-4-isopropylphenol, orthophenylphenol, methyl parahydroxybenzoate, ethyl parahydroxybenzoate, propyl parahydroxybenzoate, butyl parahydroxybenzoate, parachlorometaxylenol, parachlorometacresol, polylysine, benzalkonium chloride, didecyl dimethyl ammonium chloride, N-n-butylbenzisothiazolone, N-octylisothiazolone, 2-(4-thiazolyl)benzimidazole, methyl 2-benzimidazolylcarbamate, tetrachloroisophthalonitrile, diiodomethyl para-tolyl sulfone, parachlorophenyl-3-iodopropargyl formal, 2,3,5,6-tetrachloro-4-(methylsulfonyl) pyridine, fatty acid glycerine ester, and hinokitiol.

When the allergen-reducing composition of the present invention is used as an aerosol or spray, a water-soluble resin is preferably added in order to prevent dusting after drying. A water-soluble resin is not particularly limited, and examples thereof include polyvinyl alcohol, polyacrylic acid (or polyacrylate), polyethylene glycol, and polyvinyl pyrrolidone.

When the allergen-reducing composition of the present invention is used for eliminating house dust mite allergen, the composition may be used in combination with a miticide to further maintain the allergy-reducing effects. A miticide is not particularly limited, provided that it has the lethal or repellent effects on house dust mites. Examples of miticides that can be used include benzyl alcohol, benzyl benzoate, phenyl salicylate, cinnamaldehyde, hyssop oil, and carrot seed oil. Also, pyrethroid compounds, such as natural pyrethrin, phenothrin, or permethrin, organic phosphorus compounds such as fenitrothion, malathion, fenthion, or diazinon, dicofol, chlorobenzilate, hexythiazox, tebufenpyrad, pyridaben, or amidoflumet can be used.

When the allergen-reducing composition of the present invention is used in the form of a formulation, an emulsifier, a fixing agent, a dispersant, a stabilizer, a spray, or the like can be added according to need.

The allergen-reducing composition of the present invention can be used while being adhered or fixed to fibers or textiles.

Examples of fiber include nylon, cotton, polyester, and wool. A fiber may be a composite fiber comprising two or more of such fibers.

A textile may be in any form, provided that such product is prepared by processing the aforementioned fiber. Examples thereof include a yarn, a fabric, a texture, a woven fabric, a knitted fabric, an unwoven fabric, and a fiber web. A fiber type is not particularly limited. A textile may be in any form, for example, a clothing, interior goods such as a carpet, a sofa, a wallpaper, and a curtain, bedclothes such as an outer fabric, a comforter cover, a batting, a sheet, a pillowcase, and a mat, an automobile component such as a car seat, a car mat, a ceiling material, or a floor material, a stuffed animal, a mask, a cleaning wiper, a filter material, or a dust bag for an electric vacuum cleaner.

The allergen-reducing composition of the present invention may be adhered or fixed to fibers or textiles in that state. It is preferable that the composition be first microencapsulated and clathrated with cyclodextrin or converted into a vehicle structure and then adhered or fixed since laundry resistance of a clothing, unwoven fabric, web fiber, or the like can be imparted.

A method for adhering or fixing the composition to the fibers or textiles is not particularly limited. An example of a method is as follows.

As the allergen-reducing composition of the present invention, a treatment liquid comprising the hydroxyproline derivative represented by formula (I), a polymer thereof, or a salt of such a derivative or polymer and, according to need, a binder is used, the composition is adhered to fibers or textiles in accordance with a conventional technique, such as soaking, spraying, dispersion, or exhaustion, and the fibers or textiles is then dried. Thus, the composition can be adhered or fixed to the fibers or textiles.

In a treatment liquid, the concentration of the hydroxyproline derivative represented by formula (I) or a polymer thereof is preferably 0.1% to 5.0% (o.w.f.), and more preferably 0.5% to 2.0% (o.w.f.).

Examples of binders include acrylic ester binders such as Pararesin GH-S (Ohara Paragium Chemical Co., Ltd.), urethane binders such as Parasol PN-20 (Ohara Paragium Chemical Co., Ltd.), silicone binders such as Toray silicone BY22-826 (Toray Silicone Co., Ltd.), and fluorine and epoxy polymers. A treatment liquid preferably comprises 0.5% to 10.0% by weight of binders.

The amount of the allergen-reducing composition of the present invention to be adhered or fixed to the fibers or textiles is not particularly limited. In general, such amount is about 0.0001% to 5.0% by weight, and preferably 0.001% to 3.0% by weight on a solid basis.

A preferable example of a textile to which the allergen-reducing composition of the present invention is to be adhered or fixed is a mask. Any mask can be used, as long as it comprises, as a basic member, gauze, unwoven fabric, paper, or the like. A mask that is intended to prevent pollen inhalation is preferable, and a disposable mask is also preferable.

The allergen-reducing composition of the present invention can be adhered or fixed to a mask via, for example, a method wherein a mask basic member is soaked in a solution of an allergen-reducing composition and then dried, a method wherein the basic member is bound to the composition with the aid of a binder in accordance with a conventional technique, or a method wherein the basic member is coated with the composition via spraying or other means.

The allergen-reducing composition may be adhered or fixed to any site of the mask basic member, provided that such site covers the mouth and the nose. Preferably, the composition is adhered or fixed to the outer side of the mask.

Arginine or the like as an antibacterial agent or NOX removing agent, proline, hydroxyproline, or the like as a humectant, a fragrance, and the like may be adhered or fixed to the mask.

The allergen-reducing composition of the present invention can be adhered or fixed to, for example, a building material such as an wood building material, concrete, metal, stone, or glass, rubber, paper, resin, or plastic material, or a product comprising such material, as well as fibers or textiles, in the same manner as in the case of fibers or textiles.

With the use of the allergen-reducing composition of the present invention or fibers or textiles comprising such composition adhered or fixed thereto, allergenicity of house dust mite allergens, hair or epitheliums of pets such as dogs or cats, allergens derived from cockroaches, feather, or mold, or plant allergens such as pollens can be reduced, and a variety of allergens can be substantially eliminated.

The allergen-reducing composition of the present invention is particularly effective when allergens in the environment are house dust mite allergens or plant allergens.

EXAMPLES

Hereafter, the present invention is described in greater detail with reference to examples and test examples.

Examples 1 and 2

Allergen-Reducing Composition

Homogeneous solutions were obtained by mixing and thoroughly agitating the components shown in Table 1. The mixing ratios shown in Table 1 are expressed by weight.

TABLE 1

| Components | Example 1 | Example 2 |
| --- | --- | --- |
| N-acetyl-trans-4-hydroxy-L-proline | 1 | 0.5 |
| Polyethylene glycol (molecular weight: 20,000) | — | 0.4 |
| Ethanol | 15 | 15 |
| Ion exchanged water | 84 | 84.1 |

Example 3

Allergen-Reducing Mask

A 99.5% ethanol solution comprising 3% by weight of N-acetyl-trans-4-hydroxy-L-proline was prepared, the resulting solution was sprayed on the surfaces of a disposable mask made of an unwoven fabric (Unicharm Corporation) and of a paper disposable mask (Marusan Sangyo Co., Ltd.), and the masks were dried to prepare allergen-reducing masks. A 99.5% ethanol solution comprising 3% by weight of N-acetyl-trans-4-hydroxy-L-proline was sprayed on the intermediate filter layer of a gauze anti-pollen mask (Rohto Pharmaceutical Co., Ltd.), and the mask was dried to prepare an allergen-reducing mask. The sense of use of these masks was good.

Example 4

Allergen-Reducing Mask with Flavor

A 99.5% ethanol solution comprising 3% by weight of N-acetyl-trans-4-hydroxy-L-proline and 0.05% by weight of grapefruit flavor was prepared, the resulting solution was sprayed on the surface of an unwoven disposable mask (Unicharm Corporation), and the mask was dried to prepare an allergen-reducing mask.

Example 5

Allergen-Reducing Mask Containing NOX Adsorbent

A 99.5% ethanol solution comprising 3% by weight of N-acetyl-trans-4-hydroxy-L-proline and 1% by weight of arginine hydrochloride was prepared, the resulting solution was sprayed on the surface of an unwoven disposable mask (Unicharm Corporation), and the mask was dried to prepare an allergen-reducing mask.

Example 6

Allergen-Reducing Mask Containing Humectant

A 99.5% ethanol solution comprising 3% by weight of N-acetyl-trans-4-hydroxy-L-proline was prepared, the resulting solution was sprayed on the surface of an unwoven disposable mask (Unicharm Corporation), the mask was dried, and a 99.5% ethanol solution comprising 3% by weight of proline was sprayed on the opposite surface, followed by drying.

Example 7

Allergen-Reducing Wiper

A 99.5% ethanol solution comprising 3% by weight of N-acetyl-trans-4-hydroxy-L-proline was prepared, the resulting solution was sprayed on the surface of a disposable cleaning wiper made of an unwoven fabric (CRECIA Co., Ltd.), and the wiper was dried to prepare an allergen-reducing wiper.

Example 8

Allergen-Reducing Fabric

A 99.5% ethanol solution comprising 5% by weight of N-acetyl-trans-4-hydroxy-L-proline was prepared, a white cotton broadcloth or polyethylene terephthalate (PET) cloth was soaked therein via a padding method, and the clothes were dried at 110° C. for 2 minutes to prepare allergen-reducing fabrics.

Test Example 1

Effects of Allergen-Reducing Composition for Reducing Mite Allergen

The solutions obtained in Examples 1 and 2 (0.15 ml each) were each subjected to the reaction with 1 ml of phosphate buffer (pH 7.2) containing about 2 µg of mite allergen Derf2 contained in standard house dust. These samples were subjected to enzyme immunoassay (i.e., sandwich ELISA) to inspect the effects of reducing mite allergen Derf2.

At the outset, anti-Derf2 monoclonal antibody 15E11, which was diluted to 2 µg/ml in phosphate buffer (pH 7.4, containing 0.1% by weight of $NaN_3$) was applied to the F16 Maxisorp Nunc-Immuno Module plate (NUNC) in amounts of 100 µl per well and subjected to sensitization at 4° C. for at least 1 day. After sensitization, the liquid was removed, a blocking reagent (1% by weight of bovine serum albumin and phosphate buffer (pH 7.2, containing 0.1% by weight of $NaN_3$)) was added in amounts of 100 µl per well, and the reaction was allowed to proceed at 37° C. for 60 minutes. After the reaction, the plate was washed in phosphate buffer (pH 7.2, containing 0.1% by weight of polyoxyethylene (20) sorbitan monolaurate). Subsequently, the sample resulting from the reaction of mite allergens with the aforementioned solution was added dropwise thereto in amounts of 100 µl per well, and the reaction was allowed to proceed at 37° C. for 60 minutes.

After the reaction, the plate was washed in phosphate buffer (pH 7.2, containing 0.1% by weight of polyoxyethylene (20) sorbitan monolaurate). The peroxidase-labeled anti-Derf2 monoclonal antibody was dissolved to 200 µg/ml in distilled water, the resultant was diluted 1,000-fold with phosphate buffer (pH 7.2, containing 1% by weight of bovine serum albumin and 0.1% by weight of polyoxyethylene (20) sorbitan monolaurate), and the resulting solution was added in amounts of 100 µl per well. The reaction was allowed to proceed at 37° C. for 60 minutes, and the plate was first washed with phosphate buffer (pH 7.2, containing 0.1% by weight of polyoxyethylene (20) sorbitan monolaurate) and then with distilled water. Ortho-phenylenediamine dihydrochloride (26 mg tablet, Sigma Chemical Co.) and a hydrogen peroxide solution (13 µl) were added to 13 ml of 0.1 mol/l phosphate buffer (pH 6.2), the resultant was added in amounts of 100 µl per well, and the reaction was allowed to proceed at 37° C. for 5 minutes. Immediately thereafter, 50 µl each of 2 mol/l $H_2SO_4$ was introduced so as to terminate the reaction, and the absorbance (OD 490 nm) was assayed using a microplate spectrophotometer (Bio-Rad Laboratories Inc.)

The results are shown in Table 2.

TABLE 2

| Sample | Mite allergen concentration (ng/ml) | Reduction (%) |
| --- | --- | --- |
| None | 530 | — |
| Example 1 | 6 | 99 |
| Example 2 | 100 | 81 |

Test Example 2

Effects of Processed Fiber for Reducing Mite Allergen

The allergen-reducing fabric obtained in Example 8 was tested in terms of the effects of allergen reduction. As a control, a white cotton broadcloth and polyethylene terephthalate (PET) cloth were soaked via a padding method in an aqueous solution of 5% tannic acid (an equivalent of JP Patent Publication (kokai) No. 61-44821 A (1986)), the clothes were dried at 110° C. for 2 minutes, and the resultants were tested in terms of the effects of allergen reduction.

The clothes (5 cm×5 cm each) were introduced into reclosable plastic bags, 1 ml of phosphate buffer (pH 7.2) of mite allergen was added thereto, and the resultants were allowed to stand for 1 hour. The centrifuged samples were subjected to enzyme immunoassay (i.e., sandwich ELISA) in the same manner as in Test Example 1 to inspect the effects of reducing mite allergen Derf2.

Also, the appearances of the clothes were observed to examine the color change of the clothes.

The results are shown in Table 3.

TABLE 3

| Fabric | Sample | Mite allergen concentration (ng/ml) | Reduction (%) | Appearance |
|---|---|---|---|---|
| Cotton broadcloth | Not treated | 720 | — | White |
| | Treated with N-acetyl-trans-4-hydroxy-L-proline | 3.5 | 99.5 | White |
| | Treated with tannic acid | 120 | 83 | Light brown |
| PET cloth | Not treated | 970 | — | White |
| | Treated with N-acetyl-trans-4-hydroxy-L-proline | 2.3 | 99.8 | White |
| | Treated with tannic acid | 190 | 80 | Light brown |

All publications, patents, and patent applications cited herein are incorporated herein by reference in their entirety.

What is claimed is:

1. A method for reducing an amount of allergen, comprising the steps of:

selecting an allergen-reducing composition comprising a hydroxyproline derivative represented by formula (I):

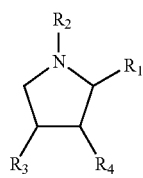

wherein $R_1$ represents hydrogen, carboxy or acyl; $R_2$ represents hydrogen or acyl; and $R_3$ and $R_4$ each independently represent hydrogen or hydroxy, provided that either $R_3$ or $R_4$ represents hydroxy, or a salt of such a derivative; and directly contacting the allergen with the composition before the allergen enters a human body by inhalation, wherein the contacting of the allergen with the composition results in a reduction in the amount of the allergen entering said human body.

2. The method according to claim 1, wherein the allergen is derived from at least one member selected from the group consisting of mites, plants, pets, cockroaches, feather and molds.

3. A method for preparing a material or product capable of reducing an amount of ambient allergen, comprising the steps of:

selecting an allergen-reducing composition comprising a hydroxyproline derivative represented by formula (I):

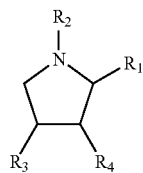

wherein $R_1$ represents hydrogen, carboxy, acyl, or alkoxycarbonyl; $R_2$ represents hydrogen or acyl; and $R_3$ and $R_4$ each independently represent hydrogen or hydroxy, provided that either $R_3$ or $R_4$ represents hydroxy, or a salt of such a derivative; and allowing such composition to adhere or fix on at least one member selected from the group consisting of a fiber, a textile, a building material, rubber, paper, resin and plastic.

4. A method for imparting a function of reducing an amount of ambient allergen, comprising the steps of:

selecting an allergen-reducing composition comprising a hydroxyproline derivative represented by formula (I):

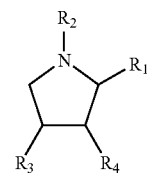

wherein $R_1$ represents hydrogen, carboxy, acyl, or alkoxycarbonyl; $R_2$ represents hydrogen or acyl; and $R_3$ and $R_4$ each independently represent hydrogen or hydroxy, provided that either $R_3$ or $R_4$ represents hydroxy, or a salt of such a derivative; and allowing such composition to adhere or fix ex vivo on an object.

5. The method according to claim 1, wherein $R_1$ represents carboxy; $R_2$ represents acetyl; $R_3$ represents hydroxy; and $R_4$ represents hydrogen.

6. The method according to claim 1, wherein the content in said composition of the hydroxyproline derivative represented by formula (I), a polymer thereof, or a salt of such a derivative or polymer is 0.01% to 30% by weight.

7. The method according to claim 1, wherein the allergen-reducing composition further comprises at least one member selected from the group consisting of a nonionic surfactant, an anionic surfactant, a cationic surfactant, a fungicide, an antibacterial agent, a miticide, an NOX removing agent, a humectant, a fragrance and a binder.

8. The method according to claim 3, wherein $R_1$ represents carboxy; $R_2$ represents acetyl; $R_3$ represents hydroxy; and $R_4$ represents hydrogen.

9. The method according to claim 3, wherein the content in said composition of the hydroxyproline derivative represented by formula (I), a polymer thereof, or a salt of such a derivative or polymer is 0.01% to 30% by weight.

10. The method according to claim 3, wherein the allergen-reducing composition further comprises at least one member selected from the group consisting of a nonionic surfactant, an anionic surfactant, a cationic surfactant, a fungicide, an antibacterial agent, a miticide, an NOX removing agent, a humectant, a fragrance and a binder.

11. The method according to claim 4, wherein $R_1$ represents carboxy; $R_2$ represents acetyl; $R_3$ represents hydroxy; and $R_4$ represents hydrogen.

12. The method according to claim 4, wherein the content in said composition of the hydroxyproline derivative represented by formula (I), a polymer thereof, or a salt of such a derivative or polymer is 0.01% to 30% by weight.

13. The method according to claim 4, wherein the allergen-reducing composition further comprises at least one member selected from the group consisting of a nonionic surfactant, an anionic surfactant, a cationic surfactant, a fungicide, an antibacterial agent, a miticide, an NOX removing agent, a humectant, a fragrance and a binder.

* * * * *